United States Patent [19]

Kyo et al.

[11] 4,122,291
[45] Oct. 24, 1978

[54] METHOD FOR THE PRODUCTION OF ALKEN-2-OL-1 OR OF ALKEN-2-OL-1 AND ALKANOL-1

[75] Inventors: Sunao Kyo; Tsumoru Renge; Hidetsugu Tanaka, all of Kashima, Japan

[73] Assignee: Kuraray Co., Ltd., Kurashiki, Japan

[21] Appl. No.: 803,889

[22] Filed: Jun. 6, 1977

[30] Foreign Application Priority Data

Jun. 8, 1976 [JP] Japan .................................. 51-67920
Sep. 30, 1976 [JP] Japan ................................ 51-117984

[51] Int. Cl.$^2$ ........................ C07C 29/12; C07F 5/04; C07D 309/06; C07D 309/18
[52] U.S. Cl. ........................... 568/887; 260/345.9 R; 260/462 R; 568/828; 568/829; 568/857; 568/858
[58] Field of Search ........... 260/639 B, 642 A, 642 E, 260/462 R, 631 B, 635 R, 617 R, 345.9 R

[56] References Cited
U.S. PATENT DOCUMENTS

| | | | |
|---|---|---|---|
| 2,055,437 | 9/1936 | Groll et al. | 260/642 E |
| 2,537,753 | 3/1952 | O'Conner et al. | 260/639 B |
| 3,028,431 | 4/1962 | Webb | 260/642 E |
| 3,117,153 | 1/1964 | Aldridge et al. | 260/639 B |
| 3,188,354 | 6/1965 | Roming | 260/639 B |
| 3,244,752 | 4/1966 | Eschinasi | 260/462 R |
| 3,407,227 | 10/1968 | Beck et al. | 260/642 E |
| 3,655,735 | 4/1972 | Pommer et al. | 260/642 A |
| 3,974,504 | 3/1976 | Kyo et al. | 260/639 B |

*Primary Examiner*—Joseph E. Evans
*Attorney, Agent, or Firm*—Bacon & Thomas

[57] ABSTRACT

Production of an alken-2-ol-1, or of an alken-2-ol-1 and an alkanol-1 from the corresponding alken-3-ol-1 is described. The above compound or compounds can be produced with good selectivity by converting an alken-3-ol-1 to the boric acid ester, and, then, contacting the ester with a palladium catalyst in the presence of hydrogen or, alternatively, by carrying out the latter-mentioned step under conditions favorable to the formation of said boric acid ester and, thereafter, subjecting the reaction product to solvolysis.

40 Claims, No Drawings

METHOD FOR THE PRODUCTION OF ALKEN-2-OL-1 OR OF ALKEN-2-OL-1 AND ALKANOL-1

This invention relates to a method of converting an alken-3-ol-1 to an alken-2-ol-1, or to an alken-2-ol-1 and an alkanol-1.

For the isomerization of an unsaturated alcohol, it is a well-known procedure to employ a carbonyl compound of a metal of Group 8 of Periodic Table of the Elements as a catalyst. However, as mentioned, for example, in Chem. Comm. 97 (1968) and J. Am. Chem. Soc. 85, 1549 (1963), such catalysts have the ability to isomerize an alken-2-ol-1 to the saturated aldehyde and, therefore, are not particularly suitable for the production of an alken-2-ol-1 via the isomerization of an alken-3-ol-1. To improve on this disadvantage, a method was proposed as in Japanese Patent Publication No. 7408/1973 (corres. to U.S. Pat. No. 3,655,735, German Pat. No. 1,643,709 and British Pat. No. 1,183,128), for instance, in which the isomerization is carried out with a metal carbonyl compound in the presence of a basic substance. However, it is still difficult, by such a method, to accomplish commercially satisfactory yield and selectivity. Whilst it is feasible, to a certain extent, to isomerize an unsaturated alcohol by mere heating without the aid of a catalyst [Canadian J. Chem. 46, 2225 (1968)], such practice requires an extremely high reaction temperature which could decompose the starting material compound or/and induce side reactions leading to a partial resinization of the material. An alternative method has also been proposed in which an alken-3-ol-1 compound is isomerized to the corresponding alken-2-ol-1 compound in the presence of palladium metal or a compound thereof and of hydrogen (Bergian Pat. No. 744,410, corres. to U.S. Pat. No. 3,697,580 and German Pat. No. 1,901,709). This method may be advantageous in that it does not involve the use of a catalyst, e.g. a metal carbonyl compound, which is not necessarily convenient to handle. However, our studies have shown that in the isomerization of an alken-3-ol-1 to an alken-2-ol-1, such as the isomerization of 3-methyl-3-buten-1-ol to 3-methyl-2-buten-1-ol, significant amounts of low-boiling compounds such as the hydrocarbon, aldehyde, etc. and certain structurally unelucidated high-boiling compounds are formed as byproducts.

The hydrocarbon and aldehyde which are byproduced in the isomerization reaction of an alken-3-ol-1 in the presence of a palladium catalyst are believed to originate from the undesirable reactions such as hydrogenolysis and isomerization which the isomerization product alken-2-ol-1 undergoes in succession under the conditions of reaction. M. Freifelder states in his Practical Catalytic Hydrogenation (John Wiley & Sons Inc., 1971) at pages 390–394 that the allyl-oxygen bond in the allylic alcohol, ester or ether is cleaved by a palladium catalyst. According to J. Jap. Chem. Soc., 1974, 1152–1153 and Collection Czechoslov. Chem. Commun. 37, 460 (1972), an allylic alcohol is isomerized to the corresponding saturated aldehyde by a palladium-on-carbon catalyst in the presence of hydrogen.

It is an object of this invention to provide an improved method of converting an alken-3-ol-1 to the corresponding isomerization product alken-2-ol-1, or to said alken-2-ol-1 and the corresponding hydrogenation product alkanol-1, substantially without accompaniment of secondary reactions giving rise to the formation of aldehyde, hydrocarbon and other byproducts. It has been found that the above object can be accomplished by converting an alken-3-ol-1 of the following general formula (I) to the boric acid ester, then contacting it with palladium metal and/or a palladium compound in the presence of hydrogen and finally subjecting the resultant boric acid ester to solvolysis to obtain the corresponding alken-2-ol-1 or said alken-2-ol-1 and the corresponding alkanol-1.

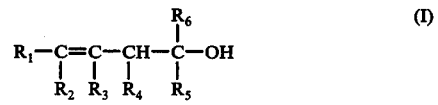

(wherein $R_1$, $R_2$, $R_3$, $R_4$, $R_5$ and $R_6$ are the same or different members selected from the group consisting of hydrogen atom and aliphatic, alicyclic and aromatic residues; any optional two members of $R_1$, $R_2$, $R_3$, $R_4$, $R_5$ and $R_6$ may form an alicyclic structure as taken together with the intervening carbon atom or atoms.) A substantially similar result is obtained when a boric acid compound is allowed to be present in the reaction system where the alken-3-ol-1 of general formula (I) is contacted with palladium and/or a palladium compound in the presence of hydrogen.

In the method of this invention, the occurence of secondary reactions other than the isomerization of the starting material compound to the alken-2-ol-1 and the hydrogenation of said starting material to the corresponding alkanol-1 are drastically suppressed. This result is surprising in view of the fact that even if 3-methyl-3-buten-1-ol in the form of acetic acid ester is contacted with a palladium catalyst in the presence of hydrogen, the isomerization reaction is accompanied by the formation of significant amounts of hydrocarbon and acetic acid as products of hydrogenolysis with the result that the combined selectivity of the reaction for the desired 3-methyl-2-buten-1-ol acetate ester and 3-methylbutanol-1 acetate ester cannot be as high as might be desired.

As regards the alken-3-ol-1 of general formula (I) which is the starting material compound in the method of this invention, $R_1$, $R_2$, $R_3$, $R_4$, $R_5$ and $R_6$ are desirably hydrogen, a saturated aliphatic hydrocarbon residue of 1 to 10 carbon atoms or a alicyclic or aromatic hydrocarbon residue, which may contain functional groups such as hydroxyl or/and ether groups, provided that the sum of the numbers of carbon atoms in $R_1$, $R_2$, $R_3$, $R_4$, $R_5$ and $R_6$ is not larger than 11. As examples of such hydrocarbon residues, there may be mentioned straight-chain and branched alkyl groups such as methyl, ethyl, butyl, isoamyl, etc.; alkyl-substituted and unsubstituted cycloalkyl groups such as cyclopentyl, methylcyclopentyl, cyclohexyl, etc.; aryl groups such as phenyl, alkylphenyl, etc.; hydroxyalkyl groups such as 2-hydroxyethyl, 3-hydroxypropyl, 2-hydroxybutyl, etc.; mono- to penta-alkylene groups which are able to form a 5- to 6-membered ring where any two of $R_1$, $R_2$, $R_3$, $R_4$, $R_5$ and $R_6$ are joined together. Among the alken-3-ols-1 which are useful for the purposes of this invention are 3-buten-1-ol, 3-methyl-3-buten-1-ol, 2-methyl-3-buten-1-ol, 3-penten-1-ol, 3-methylenepentan-1-ol, 3-methyl-3-penten-1-ol, 3,7-dimethyl-3-octen-1-ol, 3-methylene-7-methyl-octan-1-ol, 3-methylenepentane-1,5-diol, 3-methylene-7-methyloctane-1,7-diol, 3-methylene-7- methoxyoctan-1-ol, 3-cyclopentyl-3-buten-1-ol, 3-methyl-5-(2,2,6-trimethylcyclohexyl)-3-penten-1-ol, 2-isopropenyl-5-methylcyclohexan-1-ol, 4-(β-hydroxyethyl)-5,6-dihydro-2H-pyran, 3,7,11-trimethyl-3-dodecen-1-ol, 3-benzyl-3-butene-1-ol, etc.

In accordance with this invention, an alken-3-ol-1 of the above general formula (I) is first contacted with a palladium catalyst in the presence of hydrogen, either in the form of its boric acid ester or in the presence of a boric acid compound, and thereafter the resultant product is solvolyzed to obtain, as the isomerization product, an alken-2-ol-1 of the following general formula (II) and, as the hydrogenation reaction product, an alkanol-1 of the following general formula (III).

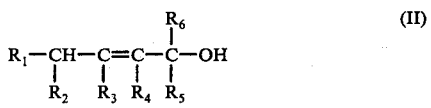

(wherein $R_1$, $R_2$, $R_3$, $R_4$ $R_5$ and $R_6$ are as hereinbefore defined)

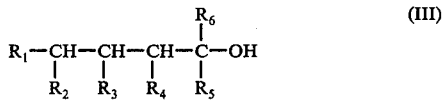

(wherein $R_1$, $R_2$, $R_3$, $R_4$ $R_5$ and $R_6$ are as hereinbefore defined)

The yield ratio of said alken-2-ol-1 to said alkanol-1 or vise versa may be altered as desired within certain limits by varying the conditions under which said alken-3-ol-1 ester is contacted with a palladium catalyst in the presence of hydrogen or said free alken-3-ol-1 is contacted with a palladium catalyst in the presence of hydrogen and a boric acid compound. For example, the aforesaid yield ratio may be varied by controlling the factors which govern the amount of dissolution of hydrogen in the liquid medium such as the reaction temperature and hydrogen pressure, the factors that govern the rate of diffusion and/or issolution of hydrogen such as the depth of liquid medium, effect of agitation, etc., or/and the factors responsible for the very hydrogenating activity of the catalyst used. Thus, the yield ratio of alken-2-ol-1 may be increased and the alken-2-ol-1 may be obtained with a substantially increased selectivity by following one or more of the procedure of reducing the amount of dissolution of hydrogen, the procedure of reducing the diffusion and/or dissolution rate of hydrogen and the procedure of suppressing the hydrogenation activity of the catalyst itself.

The method of this invention will hereinafter be described in further detail.

(A) The method comprising: conversion of alken-3-ol-1 to the boric acid ester, isomerization and hydrogenation, and solvolysis (i) Preparation of the boric acid ester of an alken-3-ol-1

The conversion of an alken-3-ol-1 to the boric acid ester can be easily accomplished simply by admixing the alken-3-ol-1 with a boric acid compound, for example, boric acid, boric anhydride, metaboric acid or any other oxy-acid of boron or an anhydride thereof or an aliphatic, alicyclic or aromatic ester of boric acid such as methyl borate, ethyl borate, butyl borate, methyl metaborate, cyclohexyl metaborate, mentyl borate or phenyl borate [e.g. Ind. Eng. Chem., 49 [2], 174(1957); J.Am. Chem. Soc. 77, 1578(1955), H. Steinberg, Organoboron Chemistry Vol. 1 (1964, John Wiley & Sons, Inc.), pp. 34–63 and U.S.P. No. 3853941]. The boric acid ester of an alcohol is produced upon mere admixture with and dissolution of the boric acid compound in the alcohol. Taking an orthoboric acid compound as an example, this reaction may be written as follows.

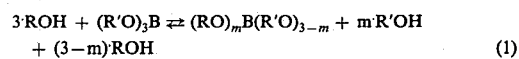

(wherein R is an alcohol residue; R' is hydrogen or an alcohol residue; m is 1, 2 or 3)

The above reaction equation represents an equilibrium reaction and, therefore, in order that a similar esterification reaction may be conducted with an alken-3-ol-1, it is necessary to remove the byproduct R'OH, i.e. water or the alcohol. In this sense, the boric acid compound used for such esterification, where it gives rise to an alcohol as it reacts, must of course be selected from among compounds such that said alcohol may be easily removed from the reaction system. Where said boric acid compound is a boric acid ester, the alken-3-ol-1, as is any other alcohol, generally takes the form of an ortho-boric acid ester or meta-boric acid ester according to its quantitative ratio to the boric acid compound. Where a boric acid compound is other than boric acid esters, the ortho-boric acid ester is produced generally when the ratio of boric acid compound to the alcohol is one-third in terms of boron atom/hydroxyl groups of the alcohol; the meta-boric acid ester is obtained when the above ratio is unity (1/1); and the condensed boric acid ester is formed when said ratio is larger than unity (>1). Stated differently, according to the above ratios, esters are formed which vary in the proportions of carbon-oxygen-boron ( C—O—B<) and boron-oxygen (—B═O, >B—O—B<) bonds.

The boric acid ester of alken-3-ol-1 may be used in any of such forms as the ortho-ester, meta-ester or a mixture of such esters, and may exist in admixture with boric acid esters of other alcohol insofar as the latter are such that they may be separated from the contemplated product alken-2-ol-1. The said boric acid ester of alken-3-ol-1 may contain one or two other alcohol residues than that of alken-3-ol-1.

(ii) The isomerization and hyrogenation of the boric acid ester of an alken-3-ol-1

The palladium and/or palladium compound used as a catalyst in the isomerization and hydrogenation of the boric acid ester of an alken-3-ol-1 according to this invention is employed within the range of 0.0005 to 5 weight percent as palladium metal based on said boric acid ester of alken-3-ol-1, preferably within the range of 0.005 to 5 weight percent and, for still better results, within the range of 0.01 to 1 weight percent on the same basis, and generally as finely dispersed in the reaction mixture. As examples of said catalyst may be mentioned such metallic palladium and salts and complex salts of palladium as palladium black, palladium powder, palladium oxide, palladium chloride, palladium nitrate, palladium sulfate and tetramine palladium chloride. These catalysts may be used either alone or as a mixture. The catalyst particularly desirable is palladium metal. Such a palladium catalyst is preferably used as supported on a suitable carrier material such as activated carbon, silica gel or the like. The catalyst support or carrier may contain water, in which case it has the advantage and convenience and ease in handling.

Hydrogen or a source of hydrogen is necessary for the isomerization of the boric acid ester of alken-3-ol-1 in the presence of such palladium catalyst. Thus, the presence of hydrogen as adsorbed on the palladium catalyst is essential to this isomerization. Therefore, hydrogen must be present in the reaction system for the purposes of this invention. The amount of hydrogen in the reaction system is not particularly critical except that a large amount of hydrogen would increase the ratio of the alkanol-1 that is a concomitant reaction product. Hydrogen may be added to the reaction system either as pure hydrogen or in admixture with an inert gas such as nitrogen, continuously or not continuously. The pressure of the isomerization reaction of this invention is not critical but since there is no particular benefit in the use of a high or low pressure, it is recommended that the atmospheric pressure of a pressure somewhat above the atmospheric pressure should be selected in consideration of the equipment and operation.

The reaction temperature may range from 0° to 250° C. and, preferably, from 30° to 200° C. The higher the reaction temperature, the greater is the yield of the desired boric acid ester of alken-2-ol-1. And this fact means that with regard to the isomerization of the double bond with a palladium catalyst, the substrate material desirably is thermally stable. The boric acid ester of alken-3-ol-1 employed according to this invention is considerably more stable than the alken-3-ol-1 as such and this fact is a clear indication of the advantage of this invention when it is contemplated to obtain an alken-2-ol-1, through the isomerization of an alken-3-ol-1. Thus, according to Minoru Imoto et al (ed.), Formaldehyde, 129 (June, 1975, Asakura Shoten), a β-hydroxyolefin, for example a 3-methyl-3-buten-1-ol, undergoes thermal decomposition through the following reaction mechanism to the corresponding olefin (isobutylene) and carbonyl compound (formaldehyde).

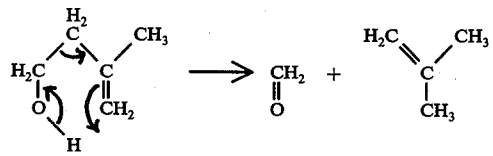

In contrast, the boric acid ester of alken-3-ol-1 employed according to this invention does not assume the cyclic transition state when shown above and, hence, is so stable thermally that it does not decompose appreciably even at an elevated temperature as high as 250° C. It is possible that the decomposition of said boric acid ester which could occur at a still higher temperature would not follow the above mechanism [J. Am. Chem. Soc. 77, 1578 (1955)].

In the isomerization and hydrogenation of the boric acid ester of alken-3-ol-1 according to this invention, the reaction may be conducted in the presence or absence of a solvent. Where the starting compound is solid at the contemplated reaction temperature, where it is desired to facilitate dispersion of the catalyst, or in order that the reaction temperature may be controlled more easily, solvent inert to the reaction may be employed. As examples of such solvent may be mentioned ethers such as diethyl ether, tetrahydrofuran, dioxane, anisole, etc.; hydrocarbons such as cyclohexane, heptane, benzene, xylene, etc; carboxylic acid esters such as ethyl acetate, methyl butyrate, isoamyl caproate, etc.; ketones such as acetone, methyl ethyl ketone, methyl isobutyl ketone, cyclohexanone, etc.; and boric acid esters such as methyl borate, ethyl borate, isoamyl borate, etc. In some cases, the presence of a solvent is conducive to the increased yield of the isomerization product relative to the hydrogenation product. While a compound having a hydroxyl group such as methanol, ethanol or butanol, or a compound containing an olefinic double bond such as cyclohexane or octene may be employed as the solvent, such practice contributes nothing to production yields and economics. Further, by allowing an oxy-acid of boron or an anhydride thereof such as boric acid, boric anhydride or metaboric acid to be present in the reaction system, the yield of the isomerization product relative to the hydrogenation product can be increased as it is the case with the presence of a solvent. The amount of such oxy-acid or anhydride may be optionally selected according to the desired yield ratio, being only limited by its saturation solubility. Whilst the reaction time primarily depends upon the reaction temperature and the available amount of hydrogen, the reaction is normally conducted for 30 to 300 minutes. With a prolonged reaction time, the relative yield of the hydrogenation product increases.

All told, the isomerization and hydrogenation reaction is conducted by maintaining the boric acid ester of alken-3-ol-1 in the presence of a palladium catalyst and hydrogen under the aforementioned conditions and, preferably, under heating.

(iii) Solvolysis of the boric acid ester of an alken-2-ol-1

The boric acid ester of alken-2-ol-1, the boric acid ester of alkanol-1 and the mixed boric acid ester of such alcohols which are produced by the above reaction can be directly solvolyzed, without prior separation from the reaction mixture, to the alken-2-ol-1, alkanol-1 and a mixture thereof, respectively. The boric acid esters of alken-2-ol-1 and alkanol-1, on contact with water or alcohol, is solvolyzed with extreme readiness and without any other chemical modification to the alken-2-ol-1 and alkanol. Therefore, in accordance with this invention, the isomerization/hydrogenation reaction mixture, either as such or after removal of the catalyst and solvent if necessary, is contacted with water, a lower alcohol such as methanol or ethanol and/or a polyhydric alcohol such as ethylene glycol or glycerin. Following this solvolysis, the unreacted alken-3-ol-1, the desired alken-2-ol-1 or/and alkanol-1 and the boric acid compound can be respectively isolated by conventional separation procedures such as fractional distillation. By way of example, where the boric acid esters of alken-2-ol-1 and alkanol-1 have been hydrolyzed, the hydrolyzate mixture is separated into an organic and an aqueous phase and the organic phase is subjected to fractional distillation. When said boric acid esters have been alcoholyzed with a lower alcohol such as methanol or ethanol, the desired product or products can be separated by removing the boric acid ester of the lower alcohol from the alcoholyzate azeotropically with the unreacted lower alcohol and subjecting the residue to fractional distillation. Where a polyhydric alcohol such as ethylene glycol or glycerin was used for the alcoholysis of said boric acid esters, the desired product may be taken out from the alcoholyzate by distilling off the desired compound, with the boric acid ester of polyhydric alcohol being separated as a distillation residue.

(B) The method in which a boric acid compound is incorporated in the reaction system for the isomerization and hydrogenation of an alken-3-ol-1.

By the method in which a boric acid compound is incorporated in the reaction system where an alken-3-ol-1 is contacted with palladium metal and/or a palladium compound in the presence of hydrogen, it is also possible to obtain a result similar to the result obtainable by the method hereinbefore described in which the alken-3-ol-1 is converted to the boric acid ester and, then, contacted with a palladium catalyst.

This method is more advantageous than the first-described method in that the step of preparing the boric acid ester of alken-3-ol-1 prior to the contacting of the alkenol with a palladium catalyst may be omitted. In this method which involves the boric acid compound present in the reaction system, too, the alken-3-ol-1 rapidly undergoes esterification with the boric acid compound added as illustrated by the equation (1) so that the reaction mixture will comprise the alken-3-ol-1, boric acid compound, the boric acid ester of alken-3-ol-1 and the water or alcohol derived from the boric acid compound in the proportions corresponding to the equilibrium composition. Although no theoretical discussion would lend any further weight to the importance of this invention, it is suspected that where such a mixture is reacted in the presence of a palladium catalyst and hydrogen, not only the double bond in the alkenol converted to the boric acid ester is selectively and preferentially isomerized and hydrogenated but due to the presence of the boric acid compound, the side reactions such as decomposition which would otherwise take place in the reaction of free alken-3-ol-1 are inhibited. Therefore, the boric acid compound to be incorporated in the reaction system according to this particular embodiment of the invention need only be a compound which is able to form an ester with the alken-3-ol-1 under the conditions of isomerization. Thus, such compound is exemplified by inorganic boric acid compounds such as boric acid, boric anhydride, metaboric acid and other oxy-acids of boron and anhydrides thereof as well as the boric acid esters of aliphatic, alicyclic, arylic and aromatic monohydric alcohols or polyhydric alcohols such as methyl borate, butyl borate, cyclohexyl metaborate, phenyl borate, 1,3,2-dioxaborolane, 1,3,2-dioxaborinane, etc. These boric acid esters may be mixed esters having mixed alcohol residues, or monoester, diester or condensed boric acid ester. From the standpoint of increasing the reaction rate, the boric acid ester of an alcohol is preferred to any inorganic boric acid compound and, for the purpose of avoiding useless isomerization reactions, the boric acid ester of a saturated alcohol, particularly a trialkyl borate, is desirably employed. The boric acid ester of a lower saturated alcohol, particularly methyl borate, is recommended in view of the ease with which the boric acid ester and product alken-2-ol-1 may be separated from each other after the reaction. The use of the boric acid ester of starting compound alken-3-ol-1 or that of end product alken-2-ol-1 or alkanol-1, or a mixture of such two or more boric acid esters is also a preferable embodiment of this invention in the sense that such practice does not introduce any heteroalcohol that would complicate the separation and recovery procedures following the reaction. The boric acid ester of alcohol may be any of the ortho-ester, meta-ester, condensed boric acid ester and a mixture of such esters. To realize the expected effect of incorporation in the reaction mixture, the amount of boric acid compound so incorporated is preferably at least equal to 20 mole percent as boric acid based on the total free hydroxyl group in the reaction system. Whilst the presence of a large amount of boric acid compound, if it be the boric acid ester of an alcohol, will not adversely affect the reaction except that the volume of the reaction system will be increased to make the operation uneconomical, the presence of an inorganic boric acid compound could result in a reduced activity of the catalyst. Generally the boric acid compound is used in a proportion ranging from 20 to 200 mole percent based on the total free hydroxyl group in the reaction system and, preferrably, within the range of 30 to 100 mole percent on the same basis. Particularly in the case of an inorganic boric acid compound, it is preferably employed in an amount from 30 to 50 mole percent.

The palladium catalyst to be incorporated in the reaction system along with said boric acid compound may be any of the catalysts that can be employed in the reaction of the boric acid ester of alken-3-ol-1 which has been described hereinbefore. The amount of such palladium catalyst may be in the range of 0.0005 to 5 weight percent, preferably 0.005 to 5 weight percent, and for still better results, 0.01 to 1 weight percent as palladium metal based on the alken-3-ol-1. Where any other isomerizable alcohol is present as the free alcohol or as a boric acid ester, the amount of said catalyst is desirably increased in accordance with the above quantitative schedule. As regards the hydrogen that is introduced into the reaction system, what has been described in connection with the isomerization and hydrogenation of the boric acid ester of alken-3-ol-1 applies as well. Thus, hydrogen may be introduced, either continuously or not continuously, as pure hydrogen or in admixture with an inert gas such as nitrogen.

The temperature and pressure of the reaction may also be similar to those described in connection with the reaction of the boric acid ester of alken-3-ol-1. The reaction solvent may also be any solvent that is employed in the reaction of such boric acid ester of alken-3-ol-1. However, where the boric acid compound to be incorporated in the reaction system is an inorganic compound, the reaction is preferably carried out at a lower temperature, for example, at a temperature in the range 0° – 150° C., and in the absence of a solvent. Although the reaction system need not be completely anhydrous, it is desirably maintained in anhydrous condition or a condition as anhydrous as possible. Thus, it should be avoided to introduce any additional water to the reaction system.

The reaction mixture obtained by the above reaction is subjected to one of the following typical treatments, either as it is or after removal of the catalyst and solvent if necessary, in order that the boric acid esters of alken-2-ol-1 and alkanol-1 present in mixture may be solvolyzed and isolated: (1) the procedure in which the mixture is contacted with an excess of water to hydrolyze the boric acid ester contained and the orgnic layer is distilled after the separation from the aqueous layer; (2) the procedure which comprises contacting the mixture with alcohol for alcoholysis and, then, subjecting the alcoholyzate to fractional distillation; (3) the procedure in which steam is introduced into the mixture to accomplish the hydrolysis and steam distillation simultaneously, and the organic layer is separated from the aqueous layer and distilled thereafter.

In this manner, the alken-2-ol-1 or the alken-2-ol-1 and alkanol-1 are separated.

The alken-2-ol-1 and alkanol-1 compounds obtainable by the foregoing method are both useful as starting materials for the synthesis of pharmaceutical and agricultural chemicals, perfumary products and other products, and are also of use as solvents and extractants.

EXAMPLE 1

The following reaction was carried out using a reaction apparatus comprising a flask fitted with a gas inlet pipe, thermometer, sampling tube, reflux condenser and electromagnetic stirrer. The above apparatus was charged with 13.15 g of the ortho-boric acid mixed ester of 3-methyl-3-buten-1-ol and 3-methylbutanol-1 (the weight ratio of 3-methyl-3-buten-1-ol to 3-methylbutanol-1 was 58:42).

After purging with nitrogen gas at a temperature of 130° C., 0.05 g of 10 wt. % palladium-on-activated carbon was added and the mixture was allowed to cool to room temperature. Then, under stirring, 160 ml of hydrogen was introduced at the same temperature to activate the catalyst. The introduction of hydrogen was suspended and the reaction mixture was heated again to 130° C. in a nitrogen atmosphere and stirred for 4 hours. A sample of the reaction mixture was taken and dissolved in benzene and, after thorough shaking with an aqueous solution of sodium hydroxide, the mixture was allowed to stand. Based on a gas chromatographic analysis of the supernatant fluid, the conversion of 3-methyl-3-buten-1-ol was 53.8% and the selectivity from 3-methyl-3-buten-1-ol to 3-methyl-2-buten-1-ol and that to 3-methylbutanol-1 were 93.1% and 5.1%, respectively. The gas chromatogram showed no peaks assignable to other products.

Control Example 1

The apparatus described in Example 1 was charged with a mixture of 12.1 g of 3-methyl-3-buten-1-ol and 0.92 g of 3-methylbutanol-1 and the reaction was carried out under the same conditions as those used in Example 1; reaction temperature 125°–135° C., 0.05 g 10 wt.% palladium-on-carbon catalyst, 100 ml of activating hydrogen, reaction time 5 hours. The results obtained were: conversion of 3-methyl-3-buten-1-ol 61.7%; selectivity from 3-methyl-3-buten-1-ol to 3-methyl-2-buten-1-ol 48.1%; selectivity to 3-methylbutanol-1 1.5%. The gas chromatogram indicated the formation of 2-methylbutane, 2-methyl-2-butene, 3-methylbutyraldehyde, etc. in significant amounts.

CONTROL EXAMPLE 2

The reaction procedure of Example 1 was repeated except that 13.7 g of 3-methyl-3-buten-1-ol acetate was used. The reaction temperature and time were as follows: 130° C. for 4 hours and, thereafter, 140° C. for 2 hours. The reaction mixture was analyzed by gas chromatography and the acetic acid content of the reaction mixture was determined by neutralization titrimetry. The results are set forth below.

| (1) | Conversion | 42.0% |
|---|---|---|
| (2) | Acetic acid formed | 0.029 mole (43.3%) |
| (3) | Selectivity for 3-methyl-2-buten-1-ol acetate (isomerization) | 69.8% |
| (4) | Selectivity for 3-methylbutan-1-ol acetate (hydrogenation) | 2.2% |

Where a similar reaction was carried out at 140° C. under the passage of hydrogen, the following results were obtained after 7 hours and after 12 hours, respectively.

|  | After 7 hours | After 12 hours |
|---|---|---|
| (1) Conversion | 57.8% | 83.7% |
| (2) Isomerization selectivity | 75.90% | 51.7% |
| (3) Hydrogenation selectivity | 2.8% | 3.0% |

EXAMPLE 2

A 5-l distilling flask fitted with a MacMahon column measuring 26 mm in inside diameter and 1500 mm long was charged with 3200 g of methyl borate and while a mixture of 452 g of 3-methyl-3-buten-1-ol, 193 g of 3-methylbutanol-1 and 500 g of 4,4-dimethyl-1,3-dioxane was fed over a period of 5 hrs from the inlet located at a height of 1200 mm from the bottom of the column with accompanying distillation. From the column top was distilled off an azeotropic mixture of methyl borate and methanol (b.p. 54.5° C., azeotropic composition - methanol 24.5 wt. %). After the charging of the mixture feed had been completed and the temperature at the column top had reached 133° C., the distillation was suspended and the bottom fraction was transferred to a 2-liter distilling flask and distilled through a Vigreux fractionating tube measuring 15 mm in inside diameter and 300 mm long, under a reduced pressure. Following the removal of 4,4-dimethy-1,3-dioxane, 625 g of the orthoboric acid mixed ester of 3-methyl-3-buten-1-ol and 3-methyl butanol-1 (b.p. 100°–103° C./1.3 mmHg) was recovered. This amount represented a yield of 98% based on the feed alcohols. A portion of boric acid ester thus obtained was hydrolyzed with an aqueous solution of sodium hydroxide and analyzed in the same manner as in Example 1. The result showed that the weight ratio of 3-methyl-3-buten-1-ol to 3-methylbutanol-1 was 70:30.

The apparatus described in Example 1 was charged with 31.37 g of the above ortho-boric acid mixed ester and a reaction similar to that of Example 1 was conducted. In this example, however, hydrogen was constantly bubbled into the mixture over the entire period of reaction, a total of 440 ml of hydrogen being used in 4 hours. The reaction mixture was treated and analyzed in the same manner as in Example 1. The conversion of 3-methyl-3-buten-1-ol was 60.6%. Based on the 3-methyl-3-buten-1-ol consumed, the selectivities for 3-methyl-2-buten-1-ol and 3-methylbutanol-1 were 75.2% and 21.2%, respectively.

EXAMPLE 3

The reaction procedure of Example 1 was repeated using 20.61 g of the same ortho-boric acid mixed ester as that used in Example 2. However, after degassing at 130° C., the reaction system was allowed to cool to room temperature and 0.04 g of the same catalyst was added. The catalyst was activated by the sparging of 450 ml of hydrogen. Then, under atmosphere of hydrogen, the reaction system was stirred for 3 hours. The reaction mixture was treated and analyzed as in Example 1. The conversion of 3-methyl-3-buten-1-ol was 73.8%. The selectivites for 3-methyl-2-buten-1-ol and 3-methylbutanol-1 were 66.4% and 30.6%, respectively, based on the 3-methyl-3-buten-1-ol consumed.

EXAMPLE 4

To an alcohol mixture of 3-methyl-3-buten-1-ol and 3-methylbutanol-1 (wt. ratio=70.5:29.5) was added a mixture of methyl borate and methanol in such a ratio that the amount of methyl borate would be equal to 2 moles per mole of the alcohol mixture. The reaction mixture was subjected to simple distillation at atmospheric pressure. The fractions boiling at liquid temperatures up to 180° C. were distilled off and a portion of the residual boric acid mixed ester was hydrolyzed with aqueous alkali and analyzed for alcohols as in Example 1. The ratio of 3-methyl-3-buten-1-ol to 3-methylbutanol-1 to methanol was 62:26:12 (by weight).

The apparatus similar to that described in Example 1 was charged with 106.7 g of the above boric acid mixed ester and the reaction was carried out using 0.13 g of 5 wt.% palladium-on-carbon. However, during the reaction, hydrogen was bubbled into the reaction system at a rate of 150 ml/hour. After a predetermined time of reaction, the reaction mixture was allowed to stand and the supernatant fluid was withdrawn. The apparatus was charged with a freshly purged material and the reaction was carried out again. In this manner, the reaction was conducted for a total of 3 times. The results obtained are set forth in the following table.

|  | 1st reaction | 2nd reaction | 3rd reaction |
|---|---|---|---|
| Residue after withdrawal of supernatant (g) | — | 5.5 | 5.1 |
| Starting material feed (g) | 106.7 | 108.5 | 107.6 |
| Reaction temperature (° C)/reaction time (hr) | 100/2 | 100/1 | 100/1.5 |
| Conversion of 3-methyl-3-buten-1-ol (%) | 64.4 | 62.5 | 63.7 |
| Selectivity for 3-methyl-2-buten-1-ol (%) | 86.8 | 81.9 | 83.5 |
| Selectivity for 3-methylbutanol-1 (%) | 13.2 | 13.6 | 15.5 |

EXAMPLES 5 to 7

The same ortho-boric acid mixed ester of alcohols as that used in Example 2 was reacted as in Example 2 except that the reaction time and temperature were varied as shown in the following table. The results are also set forth in the table.

|  | Example 5 | Example 6 | Example 7 |
|---|---|---|---|
| Reaction temperature(° C) | 22 | 100 | 130 |
| Reaction time | 80 min. | 60 min. | 120 min. |
| Conversion of 3-methyl-3-buten-1-ol (%) | 46.8 | 44.0 | 41.2 |
| Selectivity for 3-methyl-2-buten-1-ol (%) | 68.1 | 83.2 | 89.1 |
| Selectivity for 3-methylbutanol (%) | 27.9 | 14.6 | 8.8 |

EXAMPLE 8

The apparatus described in Example 1 was charged with 26.6 g of 3-methyl-3-buten-1-ol ortho-borate and the reaction was conducted at 180° C. as in Example 1. However, during the reaction, hydrogen was continuously bubbled into the reaction system at a rate of 200 ml/hour. The results obtained after 5 hours of reaction are as follows.

| (1) Conversion | 57.8% |
|---|---|
| (2) Selectivity for 3-methyl-2-buten-1-ol | 92.5% |
| (3) Selectivity for 3-methylbutanol-1 | 5.4% |

To 17.2 g of a mixture of 2-methyl-3-buten-1-ol and 2-methyl-2-buten-1-ol (wt. ratio=87:13) was added 69 g of n-butanol ortho-borate and the resultant mixture was fed to the apparatus described in Example 1. By a procedure similar to that described in Example 1, the reaction was carried using 0.1 g of palladium black at 100° C. for 2 hours. The reaction mixture was then treated and analyzed as in Example 1. The conversion of 2-methyl-3-buten-1-ol was 61.8% and the selectivity from 2-methyl-3-buten-1-ol to 2-methyl-2-buten-1-ol was 74.7%. The yield of 2-methylbutanol-1 was 2.25 g (corresponding to 20.7% based on the converted 2-methyl-3-buten-1-ol).

EXAMPLE 10

By a procedure similar to that described in Example 4, the reaction was carried out using a 5% Lindlar catalyst at 100° C. for 2.5 hours. The above Lindlar catalyst was prepared by modifying a calcium carbonate-supported palladium catalyst with lead oxide to reduce its activity to hydrogenate double bonds. The results obtained are as follows.

| (1) Conversion of 3-methyl-3-buten-1-ol | 28.3% |
|---|---|
| (2) Selectivity for 3-methyl-2-buten-1-ol | 61.3% |
| (3) Selectivity for 3-methylbutanol | 38.4% |

EXAMPLE 11

In 30 ml of dry benzene was dissolved 10 g of the same orthoboric acid mixed ester of alcohols as that used in Example 2 and 5.0 g of boric anhydride and, with stirring, the solution was gradually heated and, then, boiled for 4 hours (internal temperature =92°–97° C.). Then, nitrogen was introduced until the liquid temperature reached 118° C., whereby the benzene was distilled off. The amount of distillate was about 25 ml. To the meta-boric acid ester solution thus obtained was added 0.03 g of a 5 wt.% palladium-on-carbon catalyst and at a constant temperature of 100° C. and with the continuous introduction of hydrogen, the mixture was stirred for 2 hours. The reaction mixture was treated and analyzed as in Example 1. The results are given below.

| (1) Conversion | 62.6% |
|---|---|
| (2) Isomerization selectivity | 86.0% |

-continued

| | |
|---|---|
| (3) Hydrogenation selectivity | 9.8% |

(1) Conversion: 62.6%
(2) Isomerization selectivity: 86.0%
(3) Hydrogenation selectivity: 9.8%

EXAMPLE 12

A mixture of 15.4 g of isopulegol, 6.2 g of ortho-boric acid and 100 ml of toluene was put in a flask fitted with a reflux condenser having a water eliminator and heated under reflux with stirring by means of an electromagnetic stirrer. With the byproduct water being withdrawn from the water eliminator, the reaction was continued for 3 hours to obtain a homogeneous clear solution. Then, with the constant introduction of nitrogen, 75 ml of toluene was distilled off. To the resultant solution of isopulegol meta-borate in toluene was added 0.03 g of 5 wt.% palladium-on-carbon, and at a constant temperature of 80° C. and with the introduction of hydrogen, the mixture was stirred for 2 hours. The reaction mixture was then treated and analyzed as in Example 1. The results obtained are as follows.

| | | |
|---|---|---|
| (1) | Conversion | 59.4% |
| (2) | Isomerization (pulegol metaborate) selectivity | 78.3% |
| (3) | Hydrogenation (menthol metaborate) selectivity | 16.9% |

EXAMPLE 13

By the same apparatus and procedure as those used in Example 12, a toluene solution of ortho-boric acid ester was prepared from 12.8 g of 4-($\beta$-hydroxy ethyl)-5,6-dihydro-2H-pyran, 50 ml of toluene and 2.07 g of ortho-boric acid. The isomerization reaction was then carried out as in Example 12 to obtain the following results. In this example, the amount of toluene distilled off was 40 ml and the isomerization temperature and time were 100° C. and 3 hours, respectively.

| | | |
|---|---|---|
| (1) | Conversion | 53.1% |
| (2) | Isomerization selectivity [4-($\beta$-hydroxyethylidenyl)-tetrahydropyrane ortho-borate] | 83.7% |
| (3) | Hydrogenation selectivity [4-($\beta$-hydroxyethyl)-tetrahydropyran ortho-borate] | 12.7% |

EXAMPLE 14

23.2 g of 3-methylenepentane-1,5-diol, 4.5 g of ortho-boric acid and 70 ml of anisole were mixed together and, in an apparatus similar to that used in Example 12, the corresponding boric acid ester was synthesized. After the reaction, the anisole was distilled off under the introduction of nitrogen. When about 60 ml of anisole had been distilled off, 0.03 g of the same catalyst as that used in Example 12 was added and with the intdoduction of hydrogen, the mixture was reacted at 150° C. for 3 hours. The reaction mixture was treated and analyzed as previously mentioned to obtain the following results.

| | | |
|---|---|---|
| (1) | Conversion | 63.1% |
| (2) | Selectivity for 3-methyl-2-pentene-1,5-diol(isomerization) | 88.7% |
| (3) | Selectivity for 3-methylpentane-1,5-diol(hydrogenation) | 7.9% |

The apparatus similar to that described in Example 1 was charged with 1950 g of the same mixed alcohol boric acid ester as that used in Example 2 and, by a procedure similar to that described in Example 4, the reactin was carried out using 2.5 g of a 5 wt.% palladium-on-carbon catalyst at 100° C. for 4 hours. After the reaction, the reaction mixture was allowed to stand in a hydrogen atmosphere for 3 hours, at the end of which time the supernatant fluid was withdrawn from a tube (the hydrogen inlet tube) fitted at a level where about 90% of the entire quantity of the liquid could be withdrawn. Then, 1750 g of a previsouly purged batch of the same starting material (boric acid ester) was fed to the apparatus from which the supernatant has been withdrawn as above, in a nitrogen atmosphere. The reaction was then conducted under the same conditions as described above. This procedure was repeated 5 times and, in a total of 6 reactions, 10.695 kg of the starting material was consumed. Whilst the conversion was almost unchanged at about 65%, there was a tendency toward increased conversion as the reaction procedure was repeated. The average results are as follows.

| | |
|---|---|
| (1) Conversion | 65.7% |
| (2) Isomerization selectivity | 80.5% |
| (3) Hydrogenation selectivity | 16.3% |

Then, the reaction fluid withdrawn was passed through a filter paper to remove the small amounts of dispersed catalyst particles. A 5-l distilling flask fitted with a packed column measuring 26 mm in inside diameter and 1500 mm long was charged with 3.5 l of methanol, and 2.4 kg of the above filtrate was fed to the column through the inlet located at a height of 1200 mm from the column bottom for 8 hours, whereby said filtrate was contacted with the methanol vapor within the column. From the column top was distilled an azeotropic mixture of methyl borate and methanol [azeotropic composition 75.5/24.5 (wt. ratio), azeotropic b.p. 54.5° C.]. After the feeding of the above filtrate had been completed and the residual methanol was mostly distilled off, the residue was subjected to distillation under reduced pressure. The results were as follows.

First cut (74° C./68 mmHg–75° C./47 mmHg), the amount of distillate 1542 g

Second cut (73.8° C./45 mmHg–51° C./12 mmHg), the amount of distillate 745 g.

Residue 51 g.

The compositions (weight percents) of the above fractions were as follows.

| Fraction | Component 3-Methylbutanol | 3-Methyl-3-buten-1-ol | 3-Methyl-2-buten-1-ol | Higher-boiling fraction |
|---|---|---|---|---|
| First cut | 57.8 | 36.3 | 4.2 | 0 |
| Second cut | Trace | Trace | 99.7 | Trace |
| Residue | — | — | 90.7 | 9.3 |

EXAMPLE 16

The following reaction was conducted in a 4-necked flask fitted with a gas inlet tube, thermometer, sampling tube, reflux condenser and electromagnetic stirrer. The above apparatus was charged with 22.6 g of 3-methyl-3-buten-1-ol ortho-borate, 8.1 g of methyl isobutyl ketone and 0.044 g of a 5 wt.% palladium-on-carbon catalyst, and in a stream of nitrogen gas and under stirring, the mixture was degassed by heating at the reflux temperature. The supply of nitrogen was terminated and the reaction was conducted at the reflux temperature (144°–146° C.) with the introduction of hydrogen at a flow rate of 10 ml per min. for 3 hours. A sample of the reaction mixture was taken, diluted with toluene, shaken well with an aqueous solution of sodium hydroxide and allowed to stand. Based on a gas chromatographic analysis of the supernatant fluid, the conversion of 3-methyl-3-buten-1-ol was 56.2%, with selectivities for 3 methyl-2-buten-1-ol and 3-methylbutanol being 93.1% and 3.8%, respectively, based on the 3-methyl-3-buten-1-ol consumed. The gas chromatogram showed no peaks assignable to other products except for a detectable peak of 3-methylbutyraldehyde.

EXAMPLES 17 to 19

The reaction of Example 16 was repeated in the same apparatus as that used in Example 16, except that the reaction temperature and time and the manner of introducing hydrogen were altered and the methyl isobutyl ketone used in Example 16 was replaced with one of the additives given in the following table. The results are also shown in the same table.

|  | Example 17 | Example 18 | Example 19 |
|---|---|---|---|
| Additives(g) | Cyclohexane 15.5 g | Methyl borate 4.8 g Methanol 2.0 g | Methyl borate 9.7 g |
| Reaction temperature (° C) | 93–95 | 94–111 | 149–152 |
| Reaction time (hr.) | 1.0 | 9.0 | 1.0 |
| Manner of introducing hydrogen | Hydrogen atmosphere | Hydrogen bubbled 10 ml/min. | Hydrogen bubbled 10 ml/min. |
| Conversion of 3-methyl-3-buten-1-ol (%) | 61.8 | 60.7 | 59.2 |
| Selectivity for 3-methyl-2-buten-1-ol (%) | 92.6 | 87.8 | 92.0 |
| Selectivity for 3-methylbutanol-1 (%) | 6.4 | 9.4 | 2.9 |

EXAMPLE 20

The apparatus described in Example 16 was charged with 25.0 g of 3-methyl-3-buten-1-ol ortho-borate and 0.096 g of a 5 wt.% palladium-on-carbon catalyst containing water absorbed (palladium-on-carbon:-water=50:50 by weight) and the mixture was degassed by heating to 60° C. in nitrogen atmosphere. Thereafter the atmosphere was replaced with hydrogen, the reaction was conducted at 60° C. for one hour. The reaction mixture was analyzed as in Example 16. The results are given below.

| (1) | Conversion | 67.4% |
|---|---|---|
| (2) | Selectivity for 3-methyl-2-buten-1-ol | 83.8% |
| (3) | Selectivity for 3-methylbutanol-1 | 15.2% |

The apparatus described in Example 16 was charged with 25.0 g of 3-methyl-3-buten-1-ol ortho-borate and a varying amount of boric acid (Table below). In a current of nitrogen, the mixture was heated to 110° C. to dissolve the boric acid. Then, 0.048 g of a 5 wt.% palladium-on-carbon catalyst was added and after the supply of nitrogen was suspended, the atmosphere was replaced with hydrogen. The reaction was then conducted at 60° C. for 1 hour. The reaction mixture was analyzed as in Example 16 and the results are shown below in the table.

|  | Example 21 | Example 22 | Example 23 |
|---|---|---|---|
| Boric acid added (g) | 0.06 | 0.53 | 1.20 |
| Conversion of 3-methyl-3-buten-1-ol (%) | 65.1 | 62.0 | 63.9 |
| Selectivity for 3-methyl-2-buten-1-ol(%) | 86.7 | 90.5 | 88.6 |
| Selectivity for 3-methylbutanol-1(%) | 13.2 | 9.0 | 10.9 |

EXAMPLE 24

Using the apparatus described in Example 16, the reaction of Example 20 was repeated except that the reaction was carried out for 4 hours in the presence of 0.058 g of palladium black as the catalyst. The results obtained are set forth below.

| (1) | Conversion | 70.6% |
|---|---|---|
| (2) | Selectivity for 3-methyl-2-buten-1-ol | 66.0% |
| (3) | Selectivity for 3-methylbutanol-1 | 31.4% |

EXAMPLE 25

A 500-ml four-necked flask fitted with a reflux condenser equipped with a drying tube, stirrer, thermometer and gas inlet tube was charged with 230 g (1.0 mole) of tri-n-butyl borate and 43 g (0.5 mole) of 3-methyl-3-buten-1-ol in nitrogen streams and the temperature was increased to 120° C. to degas the reaction mixture. After the system was allowed to return to room temperature, 0.08 g of a 5wt.% palladium-on-carbon catalyst was added and, while hydrogen was introduced from the gas inlet tube, the reaction mixture was maintained at room temperature for 5 minutes. Then, with stirring in a current of hydrogen, the mixture was heated to 100° C. and held at that temperature for 2 hours. After the reaction, the hydrogen was replaced with nitrogen and the reaction mixture was allowed to stand at room temperature for 3 hours. A sample of the supernatant fluid was dissolved in benzene, shaken vigorously with an aqueous solution of sodium hydroxide and allowed to stand. The supernatant benzene layer was analyzed by gas chromatography. The results are as follows.

| (1) | Conversion of 3-methyl-3-buten-1-ol | 62.5% |
|---|---|---|
| (2) | Selectivity for 3-methyl-2-butgen-1-ol | 79.5% |
| (3) | Selectivity for 3-methylbutanol-1 | 15.3% |

CONTROL EXAMPLE 3

The reaction of Example 25 was repeated except that tri-n-butyl borate was not employed. The supernatant liquid of the reaction mixture was analyzed by gas chromatography. The results are as follows.

| | | |
|---|---|---|
| (1) | Conversion of 3-methyl-3-buten-1-ol | 58.0% |
| (2) | Selectivity for 3-methyl-2-buten-1-ol | 55.7% |
| (3) | Selectivity for 3-methylbutanol-1 | 1.9% |

The gas chromatogram revealed the formation of substantial amounts of 2-methylbutane, 2-methyl-2-butene, 3-methylbutyraldehyde, etc.

EXAMPLES 26–28

A solenoid-stirring autoclave made of pressure-resisting glass was charged with 43.3 g of a 7:3 (by mole) mixture of 3-methyl-3-buten-1-ol and 3-methylbutanol and 48.3 g of a 1:1.25 (by mole) mixture of methyl borate and methanol. The autoclave was filled with nitrogen to a pressure of 10 kg/cm$^2$, followed by gentle purging. Then, 0.06 g of a 5 wt.% palladium-on-carbon catalyst was quickly added. Nitrogen was fed to a predetermined pressure and, after a predetermined temperature was reached, hydrogen was introduced so as to increase the pressure at that temperature by 0.5 kg/cm$^2$ and the reaction was conducted with intensively stirring. The results are shown below.

| | Example 26 | Example 27 | Example 28 |
|---|---|---|---|
| Initial pressure of N$_2$ at room temperature (kg/cm$^2$) | 4.0 | 8.0 | 2.0 |
| Total pressure at reaction temperature (kg/cm$^2$) | 7.5 | 11.8 | 8.3 |
| Reaction temperature (° C)/ reaction time (hr.) | 100/1 | 100/1 | 130/1 |
| Conversion of 3-methyl-3-buten-1-ol (%) | 47.1 | 44.3 | 35.9 |
| Selectivity for 3-methyl-2-buten-1-ol (%) | 74.0 | 77.0 | 82.0 |
| Selectivity for 3-methylbutanol-1 (%) | 23.2 | 18.9 | 15.7 |

EXAMPLE 29

By a procedure similar to that described in Example 25, the reaction was carried out using 15.4 g of isopulegol, 21.9 g of triethyl borate and 0.01 g of palladium black for 2 hours. The results are as follows.

| | | |
|---|---|---|
| (1) | Conversion of isopulegol | 57.8% |
| (2) | Selectivity for pulegol | 78.7% |
| (3) | Selectivity for menthol | 15.7% |

EXAMPLE 30

The apparatus similar to that described in Example 25 was chaged with 23.6 g of 3-methylenepentane-1,5-diol, 20 ml of diethylene glycol dimethyl ether and 7.0 g of boric anhydride and the mixture was heated in nitrogen streams with stirring. To the solution was quickly added 0.05 g of a 5 wt.% palladium-on-carbon catalyst and the nitrogen was replaced with hydrogen. The reaction was carried out at 80° C. in a current of hydrogen for 2 hours. The results are as follows.

| | | |
|---|---|---|
| (1) | Conversion of 3-methylenepentane-1,5-diol | 55.4% |
| (2) | Selectivity for 3-methyl-2-pentene-1,5-diol | 85.4% |
| (3) | Selectivity for 3-methylpentane-1,5-diol | 9.8% |

EXAMPLE 31

Using 25.6 g of 4-(β-hydroxyethyl)-5,6-dihydro-2H-pyran, 11.6 g of trimethoxyboroxine and 0.02 g of a palladium-on-carbon catalyst, the reaction was carried out in the same manner as Example 25 for 2 hours.

| | | |
|---|---|---|
| (1) | Conversion of 4-(β-hydroxyethyl)-5,6-dihydro-2H-pyran | 60.7% |
| (2) | Selectivity for 4-(β-hydroxyethylidenyl)-5,6-dihydropyran | 80.3% |
| (3) | 4-(β-hydroxyethyl)-tetrahydropyran | 16.3% |

EXAMPLE 32

Using 86 g of 3-methyl-3-buten-1-ol, 272 g of triisoamyl borate and 0.2 g of a 5 wt.% palladium-on-carbon catalyst, the reaction was carried out as in Example 25 at 150° for 3 hours. The results are as follows.

| | | |
|---|---|---|
| (1) | Conversion of 3-methyl-3-buten-1-ol | 61.9% |
| (2) | Selectivity for 3-methyl-2-buten-1-ol | 87.8% |
| (3) | Selectivity for 3-methylbutanol-1 | 8.8% |

The reaction mixture was filtered to remove the catalyst and the filtrate was mixed with 500 ml of methanol and distilled in a MacMahon column (with a reflux head) measuring 20 mm in inside diameter and 500mm long. From the column top was distilled a mixture of methyl borate and methanol as a substantially azeotropic mixture, followed by removal of the excess methanol. The small residue of boric acid compound was also distilled off as methyl borate so that no boron could be detected in the bottom fraction. Then, distillation was carried out at a reduced pressure of 40 mmHg and the resultant fractions were analyzed. The results are as follows.

| | |
|---|---|
| First cut (59° C/40 mmHg–61.7° C/40 mmHg) | |
| The amount of distillater | 98.2 g |
| Second cut (61.7° C/40mmHg–62.0° C/40 mmHg) | |
| The amount of distillate | 204.0 g |
| Residue (including column hold-up) | 44.9 g |

| Fraction | Component | 3-Methyl-butanol (wt. %) | 3-Methyl-3-buten-1-ol (wt. %) | 3-Methyl-2-buten-1-ol (wt. %) | High-boiling fraction (wt. %) |
|---|---|---|---|---|---|
| First cut | | 63.1 | 32.8 | 4.1 | 0 |
| Second cut | | 0 | 0.8 | 99.2 | 0 |
| Residue | | Trace | 0 | 95.5 | 4.5 |

The high-boiling fraction and 3-methyl-2-buten-1-ol could be separated by simple distillation to obtain 3-methyl-2-buten-1-ol in a purity of no less than 99%.

What is claimed is:

1. A method of producing alcohols selected from the group consisting of alken-2-ol-1 of general formula (II) and alkanol-1 of general formula (III) and mixtures thereof, from an alken-3-ol-1 of general formula (I):

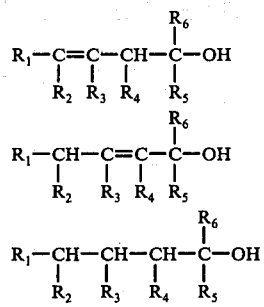

wherein $R_1$, $R_2$, $R_3$, $R_4$, $R_5$ and $R_6$, which may be the same or different, are members selected from the group consisting of hydrogen and aliphatic, alicyclic and aromatic residues and wherein any pair of $R_1$, $R_2$, $R_3$, $R_4$, $R_5$ and $R_6$ may constitute an alicyclic structure taken together with the intervening carbon atom or atoms, which comprises: converting said alken-3-ol-1 of the general formula (I) to a boric acid ester and contacting the ester with a palladium catalyst in the presence of hydrogen and subjecting the reaction product thus obtained to solvolysis.

2. The method as defined by claim 1, wherein said boric acid ester is formed by admixing the alken-3-ol-1 (I) with a boric acid compound.

3. The method as defined by claim 1, wherein said boric acid ester is formed by contacting said alken-3-ol-1 (I) with a boric acid compound in the presence of a palladium catalyst and hydrogen.

4. The method as defined by claim 1, wherein said palladium catalyst is palladium metal.

5. The method as defined by claim 1, wherein the solvent for said solvolysis is methanol.

6. The method as defined by claim 1, wherein the selectivity of the reaction for alken-2-ol-1 relative to alkanol-1 is substantially increased by suppressing the hydrogenation activity of the reaction medium.

7. The method as defined by claim 1, further comprising separating the product alken-2-ol-1 from the product alkanol-1.

8. The method as defined by claim 1, wherein the product is alken-2-ol-1 of general formula (II).

9. The method as defined by claim 1, wherein the product is a mixture of alken-2-ol-1 of general formula (II) and alkanol-1 of general formula (III).

10. A method of producing boric acid esters of alcohols selected from the group consisting of a boric acid ester of an alken-2-ol-1 of general formula (II):

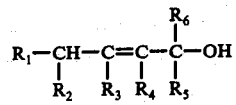

and a boric acid ester of an alkanol-1 of general formula (III):

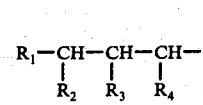

and mixtures thereof, wherein $R_1$, $R_2$, $R_3$, $R_4$, $R_5$ and $R_6$, which may be the same or different, are members selected from the group consisting of hydrogen and aliphatic, alicyclic and aromatic residues and wherein any pair of $R_1$, $R_2$, $R_3$, $R_4$, $R_5$ and $R_6$ may constitute an alicyclic structure taken together with the intervening carbon atom or atoms, which comprises: contacting a boric acid ester of an alken-3-ol-1 of general formula (I):

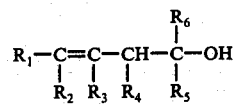

wherein $R_1$, $R_2$, $R_3$, $R_4$, $R_5$ and $R_6$ are as defined above, with a palladium catalyst in the presence of hydrogen.

11. The method as defined by claim 10, wherein said boric acid ester of alken-3-ol-1 (I) is produced in situ from said alken-3-ol-1 and a boric acid compound.

12. The method as defined by claim 11, wherein said boric acid compound is methyl borate.

13. The method as defined by claim 10, wherein said palladium catalyst is palladium metal.

14. The method as defined by claim 10, wherein said palladium catalyst is used in an amount from 0.0005 to 5 weight percent as palladium metal based on said boric acid ester of alken-3-ol-1.

15. The method as defined by claim 10, wherein said palladium catalyst is used in an amount from 0.005 to 5 weight percent as palladium metal based on said boric acid ester of alken-3-ol-1.

16. The method as defined by claim 10, wherein the contacting of said boric acid ester of alken-3-ol-1 with said palladium catalyst in the presence of hydrogen is effected at a temperature in the range of 0° to 250° C.

17. The method as defined by claim 10, wherein the product is a boric acid ester of an alken-2-ol-1 of general formula (II).

18. The method as defined by claim 10, wherein the product is a mixture of a boric acid ester of an alken-2-ol-1 of general formula (II) and a boric acid ester of an alkanol-1 of general formula (III).

19. A method of producing alcohols selected from the group consisting of an alken-2-ol-1 of general formula (II):

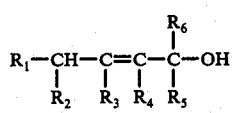

an alkanol-1 of general formula (III):

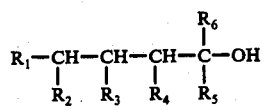

and mixtures thereof, wherein $R_1$, $R_2$, $R_3$, $R_4$, $R_5$ and $R_6$, which may be the same or different, are members selected from the group consisting of hydrogen and aliphatic, alicyclic and aromatic residues and wherein any pair of $R_1$, $R_2$, $R_3$, $R_4$, $R_5$ and $R_6$ may constitute an alicyclic structure taken together with the intervening carbon atom or atoms, which comprises:

contacting a boric acid ester of an alken-3-ol-1 of general formula (I):

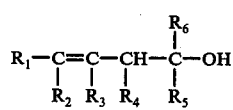

with a palladium catalyst in the presence of hydrogen and, then, subjecting the resultant reaction mixture to solvolysis.

20. The method as defined by claim 19, wherein said boric acid ester of alken-3-ol-1 is produced in situ from said alken-3-ol-1 and a boric acid compound.

21. The method as defined by claim 20, wherein said boric acid compound is methyl borate.

22. The method as defined by claim 19, wherein said palladium catalyst is palladium metal.

23. The method as defined by claim 19, wherein said palladium catalyst is used in an amount from 0.0005 to 5 weight percent as palladium metal based on said boric acid ester of alken-3-ol-1.

24. The method as defined by claim 19, wherein said palladium catalyst is used in an amount from 0.005 to 5 weight percent as palladium metal based on said boric acid ester of alken-3-ol-1.

25. The method as defined by claim 19, wherein the contacting of said boric acid ester of alken-3-ol-1 with said palladium catalyst in the presence of hydrogen is effected at a temperature in the range of 0° to 250° C.

26. The method as defined by claim 19, wherein the solvent for said solvolysis is methanol.

27. The method as defined by claim 19, wherein the product is an alken-2-ol-1 of general formula (II).

28. The method as defined by claim 19, wherein the product is a mixture of an alken-2-ol-1 of general formula (II) and an alkanol-1 of general formula (III).

29. A method of producing alcohols selected from the group consisting of an alken-2-ol-1 of general formula (II):

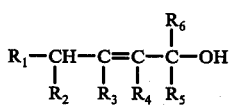

an alkanol-1 of general formula (III):

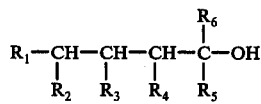

and mixtures thereof, wherein $R_1$, $R_2$, $R_3$, $R_4$, $R_5$ and $R_6$, which may be the same or different, are members selected from the group consisting of hydrogen and aliphatic, alicyclic, and aromatic residues and wherein any pair of $R_1$, $R_2$, $R_3$, $R_4$, $R_5$ and $R_6$ may constitute an aliphatic structure taken together with the intervening carbon atom or atoms, which comprises: contacting an alken-3-ol-1 of general formula (I):

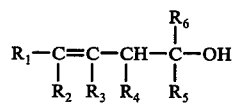

wherein $R_1$, $R_2$, $R_3$, $R_4$, $R_5$ and $R_6$ are as defined above, with a palladium catalyst in the presence of hydrogen and a boric acid compound, and, then, subjecting the reaction mixture to solvolysis.

30. The method as defined by claim 29, wherein said palladium catalyst is palladium metal.

31. The method as defined by claim 29, wherein said palladium catalyst is used in an amount from 0.0005 to 5 weight percent as palladium metal based on said alken-3-ol-1.

32. The method as defined by claim 29, wherein said palladium catalyst is used in an amount from 0.005 to 5 weight percent as palladium metal based on said alken-3-ol-1.

33. The method as defined by claim 29, wherein said boric acid compound is methyl borate.

34. The method as defined by claim 29, wherein said boric acid compound is used in an amount from 20 to 200 mole percent as boric acid based on the free hydroxyl group in the reaction system.

35. The method as defined by claim 29, wherein the contacting of said alken-3-ol-1 with said palladium catalyst is effected at a reaction temperature in the range of 0° to 150° C.

36. The method as defined by claim 29, wherein the solvent for said solvolysis is methanol.

37. The method as defined by claim 29, wherein the product is an alken-2-ol-1 of general formula (II).

38. The method as defined by claim 29, wherein the product is a mixture of an alken-2-ol-1 of general formula (II) and an alkanol-1 of general formula (III).

39. A method of producing alcohols selected from the group consisting of 3-methyl-2-buten-1-ol, 3-methylbutanol-1 and mixtures thereof, which comprises reacting 3-methyl-3-buten-1-ol with methyl borate to obtain the boric acid ester of said butenol, contacting said ester with palladium metal in the presence of hydrogen and subjecting the reaction mixture to methanolysis.

40. A method of producing alcohols selected from the group consisting of 3-methyl-2-buten-1-ol, 3-methylbutanol-1 and mixtures thereof, which comprises contacting 3-methyl-3-buten-1-ol with palladium metal in the presence of methyl borate and hydrogen and, then, subjecting the reaction mixture to methanolysis.

* * * * *